United States Patent
Morinaka et al.

(10) Patent No.: US 6,280,404 B1
(45) Date of Patent: Aug. 28, 2001

(54) ARTIFICIAL LIMB JOINT DEVICE

(76) Inventors: Yoshihiro Morinaka, 16-1, Atagomachi 2-chome, Kochi-shi, Kochi 780-0051 (JP); Takumi Hino, Sun Port Heim Sanbashi 502, 2-8, Sanbashidori 6-chome, Kochi-shi, Kochi 780-8010 (JP)

(*) Notice: Subject to any disclaimer, the term of this patent is extended or adjusted under 35 U.S.C. 154(b) by 5 days.

(21) Appl. No.: 09/170,262

(22) Filed: Oct. 13, 1998

(30) Foreign Application Priority Data

Apr. 8, 1998 (JP) .................................................. 10-096421

(51) Int. Cl.[7] ...................................................... A61F 5/00
(52) U.S. Cl. .................... 602/16; 602/5; 602/26
(58) Field of Search ................... 602/26, 27, 16, 602/23, 21

(56) References Cited

U.S. PATENT DOCUMENTS 5,242,378 * 9/1993 Baker ..................................... 602/23

* cited by examiner

*Primary Examiner*—Kim M. Lewis
(74) *Attorney, Agent, or Firm*—Armstrong, Westerman, Hattori, McLeland & Naughton, LLP

(57) ABSTRACT

An artificial limb joint device which has sufficient strength as a joint, can efficiently absorb a torsion load received from a body during walking, and can restore its original shape immediately after absorption and can adjust angle continuously. The artificial limb joint device comprising body protecting members which adjoin to each other, one of which can turn with respect to the other body protecting member, wherein the body protecting members are made from a material having flexibility, a support member for rotatably supporting the adjoining side end portion of the one body protecting member is placed on the adjoining side end portion of the other body protecting member, a stopper member which contacts a contact portion provided in the adjoining side end portion of the one body protecting member to limit the rotation angle of the body protecting member is installed on the support member, and the position of the stopper member can be changed along the rotation locus of the contact portion and controlled.

13 Claims, 14 Drawing Sheets

A

B

A

B

A

B

A

B

A

B

ARTIFICIAL LIMB JOINT DEVICE

BACKGROUND OF THE INVENTION

1. Field of the Invention

The present invention relates to an artificial limb joint device comprising body protecting members which adjoin to each other in a vertical direction and one of which can turn on an axial core in a direction perpendicular to the longitudinal direction with respect to the other body protecting member.

2. Description of the Related Art

There are generally known three different types of artificial limb joint devices shown in FIGS. 15A, B and C according to the prior art.

A first type of artificial limb joint device shown in FIG. 15A is manufactured by Fillauer Co. and makes it possible to adjust an angle between an upper body protecting member 50 and a lower body protecting member 51 continuously by interconnecting the upper body protecting member 50 and the lower body protecting member 51 by a pair of upper and lower plate-like joints 52, 53 and rotating a pair of vertical screws 55, 56 provided to a joint body 54.

A second type of artificial limb joint device shown in FIG. 15B is manufactured by USMC Co., and makes it possible to adjust an angle between an upper body protecting member 50 and a lower body protecting member 51 in increments of 5° to 10° by interconnecting the upper body protecting member 50 and the lower body protecting member 51 by a plate-like joint 57 and replacing a cam 58 for angle adjustment provided to the lower body protecting member 51 with another cam (available in seven types).

A third type of artificial limb joint device shown in FIG. 15C is manufactured by Becker Co., and makes it possible to adjust an angle between an upper body protecting member 50 and a lower body protecting member 51 in increments of 5° to 10° by interconnecting the upper body protecting member 50 and the lower body protecting member 51 by a pair of upper and lower joints 59, 60 and replacing a cam 62 for angle adjustment provided to a joint body 61 with another cam (available in seven types).

Although the first type of artificial limb joint device can eliminate the need, as in the second and third types, for replacing the cam 58 or 62 for angle adjustment and can adjust the angle continuously, it has such inconvenience that the adjustable range of the angle is narrow (about 5°). Since the upper body protecting member 50 and the lower body protecting member 51 are interconnected by a joint, these artificial limb joint devices manufactured by the above three companies have at least two connectors: a connector between the upper body protecting member 50 and the joint and a connector between the lower body protecting member 51 and the joint. Therefore, the two connectors cannot absorb a torsion load received from the body during walking, for example. As a result, the joint is used to absorb the above torsion load efficiently. However, the joint is made from a metal in most cases. When the joint is made from a metal, it has poor flexibility and hence, prevents the natural motion of a man disadvantageously.

When the joint is made from a metal, it is excellent in strength but it is hardly returned to its original shape when it is deformed by a torsion load and may not be usable any longer. Therefore, as the joint must be constructed to be strong enough to withstand long-time use, the above inconvenience becomes marked and there is room for improvement.

When a man walks, one side of the pelvis first turns at 4°, the thighbone turns at 8° relative to the pelvis, and the shinbone turns at 9° relative to the thighbone. The total turning angle of the lower limb of these three segments is about 25°. During walking, the inclination of the pelvis and hip, knee and ankle joints are used for bending and stretching. That is, the artificial limb joint device requires the knee joint and the ankle joint to turn at 9° on a horizontal plane, and the shinbone turns when the repulsion force of the bottom of a foot against the floor is used to fix a foot portion. Therefore, it is ideal that the artificial limb joint device should have flexibility to absorb torsion and it is important that the artificial limb joint device should be returned to its original shape even when it is twisted.

SUMMARY OF THE INVENTION

In view of the above circumstances, it is an object of the present invention to provide an artificial limb joint device which can absorb a torsion load received from the body during walking efficiently though it has sufficient strength as a joint, can return to its original shape immediately after absorption and can angularly adjust continuously.

The above object of the present invention can be attained by an artificial limb joint device comprising body protecting members which adjoin to each other in a vertical direction and one of which can turn with respect to the other body protecting member, wherein the body protecting members are made from a material having flexibility, a support member for rotatably supporting the adjoining side end portion of the body protecting member is placed on the adjoining side end portion of the other body protecting member, a stopper member which contacts a contact portion provided in the adjoining side end portion of the body protecting member to limit the rotation angle of the body protecting member is installed on the support member, and the position of the stopper member can be changed along the rotation locus of the contact portion and controlled.

Therefore, since the body protecting members are made from a material having flexibility, and the adjoining side end portions of the body protecting members which adjoins to each other in a vertical direction are interconnected by the support member in such a manner that they are placed one upon the other in a horizontal direction, while sufficient strength can be ensured at connectors, a torsion load received from the body during walking can be absorbed efficiently by the bending of the body protecting members, and the body protecting members can restore their original shapes by restoring force immediately when they do not receive the load. The rotation angle range of the rotating body protecting member can be adjusted continuously to a wider extent compared with prior art devices by changing the position of the stopper member along the rotation locus of the contact portion. In addition, by moving the stopper member along the rotation locus of the contact portion, the contact location between the stopper member and the contact portion is always along the rotation locus even when the position of the stopper member is changed and hence, the same force can be always applied to the stopper member from the contact portion in the same direction, thereby making it possible to make the contact state of the stopper member to the contact portion always the same. Therefore, the damage or breakage of the contact portion and the stopper member by contact therebetween can be reduced as much as possible, and the artificial limb joint device can be advantageously made durable. By changing the size of the stopper member along the rotation locus of the contact portion or providing a plurality of stopper members, the range of the rotation angle can be changed and the rotating body protecting member can be fixed so that it is completely unrotatable.

Out of the body protecting members which adjoin to each other in a vertical direction, the unrotating body protecting member, the adjoining side end portion of which does not rotate, is arranged on an inner side which is in contact with the body, the support member is installed on the outer side of the adjoining end portion of the unrotating body protecting member, and the rotating body protecting member, the adjoining side end portion of which rotates, is rotatably supported by bringing into contact with the outer side of the support member. On the contrary, when the rotating body protecting member is located on the inner side, it is sandwiched between the body and the unrotating body protecting member, whereby rotation resistance is not provided to the rotating body protecting member, the rotating body protecting member located on an outer side can turn easily and move smoothly, and a problem such as the damage of the body which occurs when the rotating body protecting member cannot follow the motion of the body which is in contact with the body protecting member can be prevented without fail.

The body protecting members consist of a thigh front cuff, a calf rear cuff and a foot sole plate, and a long lower limb joint device can be constructed by interconnecting the adjoining side end portions of these body protecting members by the support members. Alternatively, the body protecting members may consist of the calf rear cuff and the foot sole plate, and a short lower limb joint device can be constructed by interconnecting the adjoining side end portions of these body protecting members by the support members. Also, the body protecting members may consist of the thigh front cuff and the calf rear cuff, and a knee joint device can be constructed by interconnecting the adjoining side end portions of these body protecting members by the support members.

A calcaneus portion at the rear of the foot sole plate and an Achilles' tendon portion at the rear of the lower end portion of the calf rear cuff are made open. When a joint is used as in the prior art, a connector between the joint and the body protecting member must have strength and the strength of the foot sole plate cannot be reduced so much. In contrast, in the present invention, since the connector does not need to be reinforced, even when the calcaneus portion at the rear of the foot sole plate and the Achilles' tendon portion at the rear of the lower end of the calf rear cuff are made open, there is no problem with strength. The above open structure makes it possible to reduce weight, put on shoes easily and further adjust the flexibility of the foot sole plate and the calf rear cuff.

Since a flat and circular knee joint face for positioning the support member for supporting the thigh front cuff is formed at the upper end of the calf rear cuff and a flat and circular foot joint face for positioning the support member for supporting the foot sole plate is formed at the lower end of the calf rear cuff, the positioning of the support members can be carried out simply by placing the supporting members on the flat knee joint face and the foot joint face, thereby making it unnecessary to align a connection bolt hole formed in the support member and a connection bolt hole formed in the thigh front cuff or the foot sole plate. Thus, assembly work can be carried out easily and quickly.

The rotational center of the thigh front cuff is set to substantially the same height as the height in a vertical direction of the biophysiological knee joint axis when the knee joint device is constructed, the rotational center of the foot sole plate is set to substantially the same height as the height in a vertical direction of the biophysiological ankle joint axis when the short lower limb joint device is constructed, and the rotational center of the thigh front cuff is set to substantially the same height as the height in a vertical direction of the biophysiological knee joint axis and the rotational center of the foot sole plate is set to substantially the same height as the height in a vertical direction of the biophysiological ankle joint axis when a long lower limb joint device is constructed. Thereby, the rotational centers of the joint axes of the body and the thigh front cuff and the rotational center of the foot sole plate or the like can be made substantially the same and hence, the joint axes of the body can move easily.

The support members are made of a plate-like body fixed to the upper and lower end portions of the calf rear cuff, fixing tools for fixing the stopper members whose lower ends are mated with a slide groove formed like an arc on the surface of this plate-like body in such a manner that they can move along the slide groove and cannot move over the plate-like body are provided to move the stopper members along the slide groove. Thus, the stopper members can be moved smoothly in the form of an arc and controlled.

The fixing tools consist of a headed screw having a hexagonal hole formed in the center of an axial portion and a nut to be mated with the end of the headed screw, a through hole into which the axial portion of the headed screw is inserted is formed in the support member, a threaded portion to be mated with the axial portion of the headed screw is formed in the stopper member, the end of the axial portion of the headed screw is inserted from the front side into the support member from the rear side and mated with the stopper member, and the nut is mated with the end of the axial portion projecting from the stopper member.

That is, the end of the axial portion of the headed screw is inserted into the support member from the rear side, a wrench or the like is inserted into the hexagonal hole formed in the center of the axial portion and turned counterclockwise to mate the support member with the stopper member. The stopper member can be brought close to the head portion of the headed screw and the stopper member is pressed against and fixed to the support member by this mating. After fixing, the nut is mated with the end of the axial portion of the headed screw projecting to the front side from the stopper member by rotating the nut clockwise, in other words, dextrogyrately, to prevent the loosening of the headed screw by the nut without fail.

The adjoining side end portions of the thigh front cuff and the foot sole plate are formed like an arc so that they can enter an arc space formed on an inner side of the stopper member projecting upward from the slide groove, and the contact portion which projects into a traveling path of the stopper member and contacts the stopper member is formed integrally with at least one of the right and left end portions of each of the arc adjoining side end portions.

Therefore, the adjoining side end portions of the thigh front cuff and the foot sole plate can be inserted into the arc space formed on the inner side of the upper end of the stopper member. The contact portion contacting the stopper member is formed integrally with at least one of right and left end portions of the arc adjoining side end portion.

The stopper members located at the lower end portion of the calf rear cuff, out of the stopper members mated with the slide grooves, includes a fan-like stopper member having a width of 115°, a backward turning angle adjustable range of 11° and a forward turning angle of 18°, a fan-like stopper member having a width of 65°, a backward turning angle adjustable range of 11° and a forward turning angle of 18° and a fan-like stopper member for further fixing these two stopper members, having a width of 40° and an adjustable range of 12°, these three types of stopper members are used alone or in combination of two or more, or a plurality of stopper members of the same type are used to switch among a state for carrying out only backward damping, a state for carrying out only forward damping, a state for carrying out both forward and backward dampings and a fixed state for preventing the rotation of the rotating body protecting member, and the stopper member located at the upper end portion of the calf rear cuff, out of the stopper members mated with the slide grooves, is consisted of a fan-like stopper member for damping the extension of the knee and having a width of 105°, a bending angle of 30° and an over-extension angle of 10°.

BRIEF DESCRIPTION OF THE DRAWINGS

The above and other objects, features and advantages of the present invention will become more apparent from the following detailed description when taken in conjunction with the accompanying drawings wherein:

FIGS. 2A to 2C are diagrams showing the shape of each member constituting the artificial limb joint device, wherein FIG. 2A shows that a calf rear cuff is attached, FIG. 2B shows that a thigh front cuff and a foot sole plate are attached, and FIG. 2C shows that the thigh front cuff, the calf rear cuff, and the foot side plate are attached;

FIGS. 10A and 10B show other artificial limb joint devices, wherein FIG. 10A shows a short lower limb joint device and FIG. 10B shows a knee joint device;

FIGS. 12A and 12B show the support member of FIG. 10, wherein FIG. 12A shows a plan view and FIG. 12B is a bottom view of the support member;

FIG. 15C is a perspective view of these joint devices.

DETAILED DESCRIPTION OF THE PREFERRED EMBODIMENTS

Figure 1:
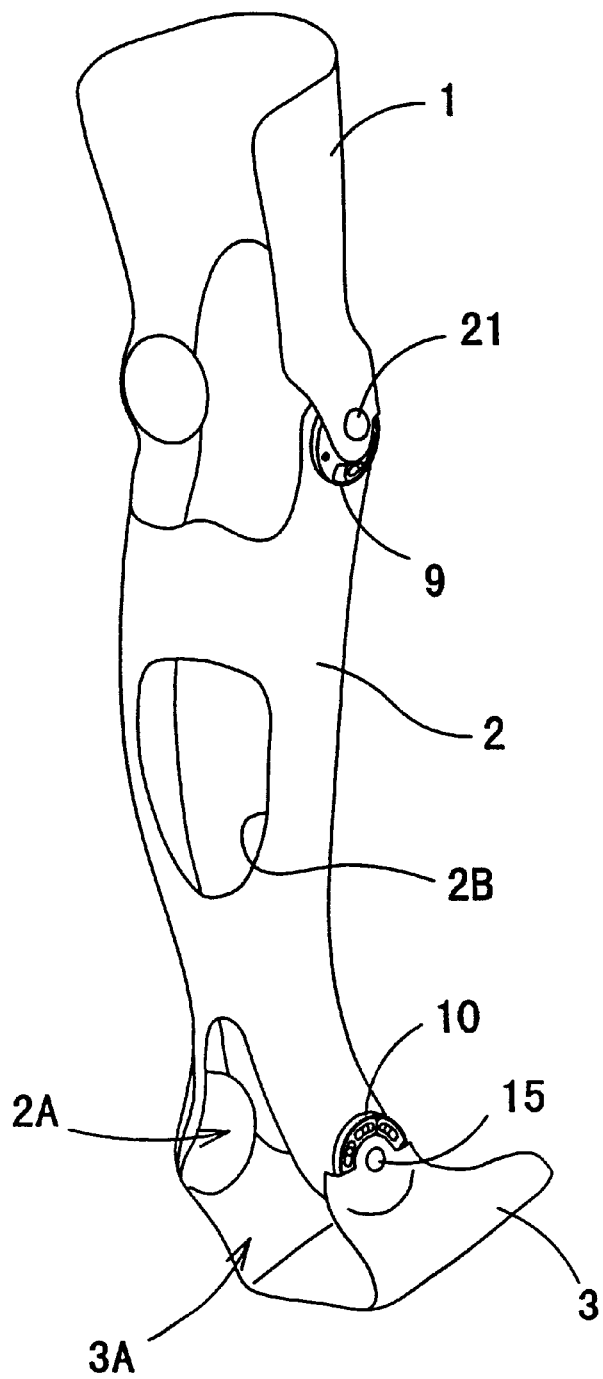
FIG. 1 is a perspective view of an artificial limb joint device.
Figure 2:
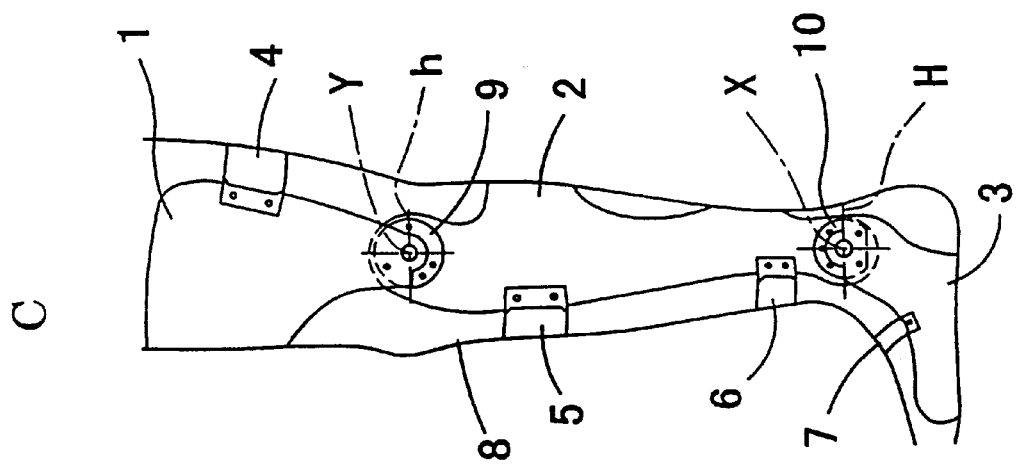
Figure 2:
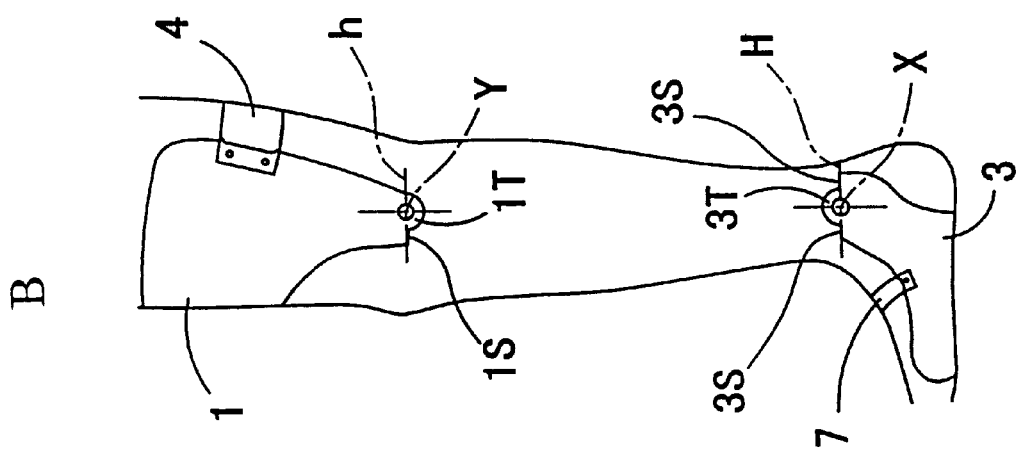
Figure 2:
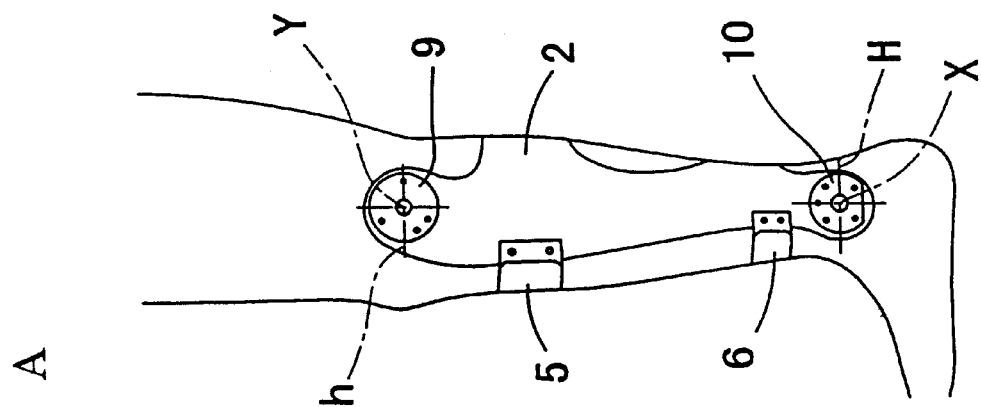

FIG. 1 shows an artificial limb joint device according to the present invention. This artificial limb joint device comprises as main constituting members three body protecting members—a thigh front cuff 1, a calf rear cuff 2 and a foot sole plate 3—from above, and the thigh front cuff 1, the calf rear cuff 2 and the foot sole plate 3 which adjoin to one another in a vertical direction are connected to one another. FIG. 2C shows that this artificial limb joint device is attached and a lower limb 8 is fixed to the artificial limb joint device by four belts 4, 5, 6, 7 shown in an upper part of the figure. To make more clear the shapes of the above three body protecting members 1, 2, 3, FIGS. 2A and 2B show that only specific body protecting members are attached. That is, FIG. 2A shows that the calf rear cuff 2 is attached and FIG. 2B shows that the thigh front cuff 1 and the foot sole plate 3 are attached.

The thigh front cuff 1, the calf rear cuff 2 and the foot sole plate 3 are made from various synthetic resins such as polyethylene or those synthetic resins into which another substance such as synthetic rubber or metal is mixed to provide flexibility, thereby making it possible to reduce weight. In addition, they are free from deformation and modification caused by fatigue due to long-time use, can absorb a torsion load received from the body during walking efficiently and can be restored to their original shapes when the load is not applied.

As shown in FIG. 1, an Achilles' tendon portion 2A at the rear of the lower end portion of the above calf rear cuff 2 and a calcaneus portion 3A at the rear of the foot sole plate 3 are made open, thereby making it possible to reduce the weight of the whole artificial limb joint device, to put on shoes easily and further to adjust the flexibility of the calf rear cuff 2 and the foot sole plate 3. In the figure, the shoes are not shown. Denoted by 2B in the figure is an opening formed in the center portion in a vertical direction of the above calf rear cuff 2, thereby making it possible to reduce the weight of the whole artificial limb joint device.

As shown in FIG. 1 and FIG. 2B, support members 9, 10 for rotatably supporting the adjoining side end portions of the thigh front cuff 1 and the foot sole plate 3 which are located above and below the calf rear cuff 2 in a vertical direction are attached to the upper end portion and lower end portion of the calf rear cuff 2, respectively. A description is subsequently given of connection structures for connecting the calf rear cuff 2 to the thigh front cuff 1 and the foot sole plate 3.

Figure 3:
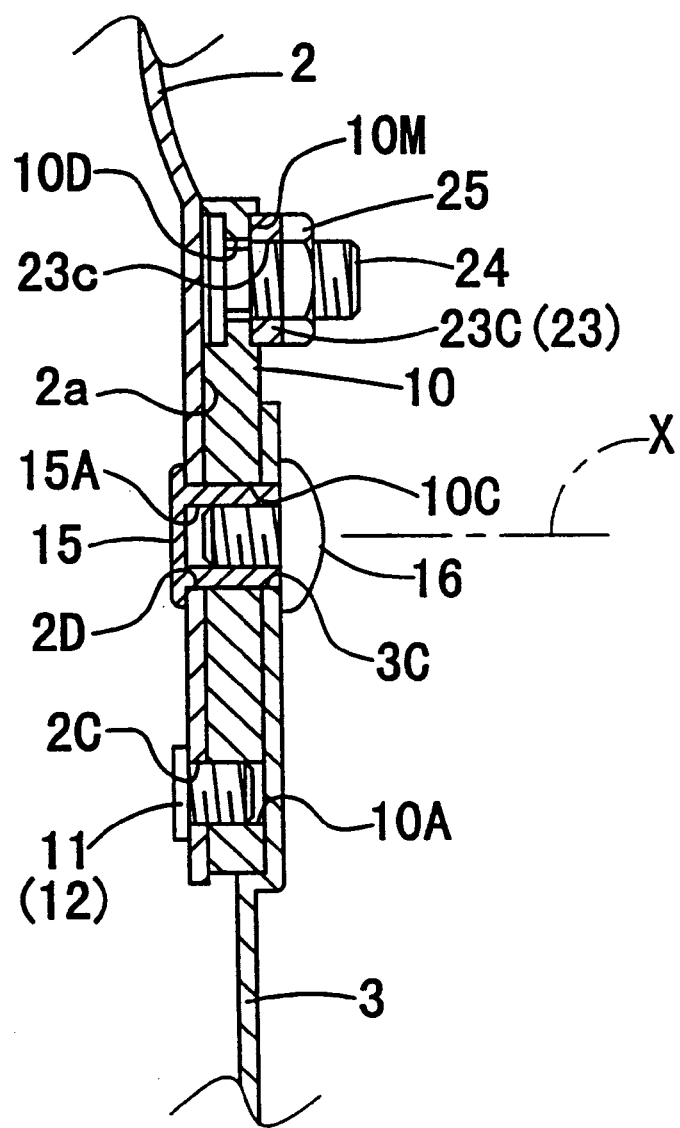
FIG. 3 is a longitudinal side view showing a connector between the calf rear cuff and the foot sole plate.
Figure 5:
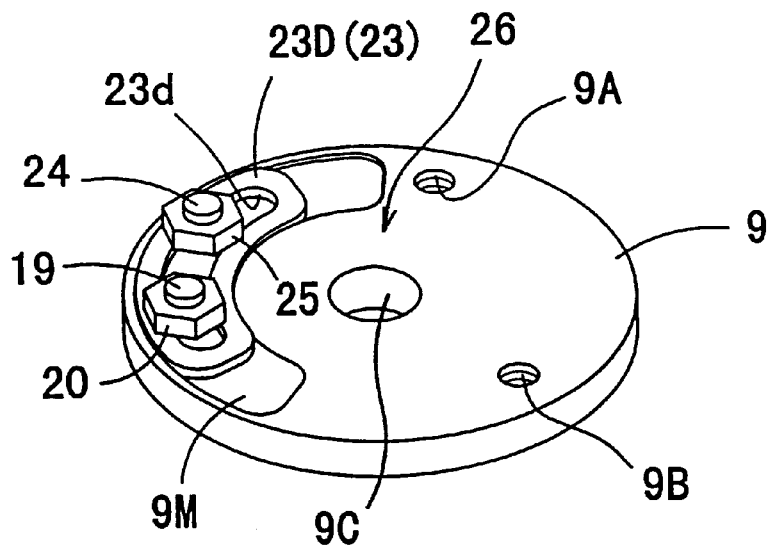
FIGS. 5A and 5B are perspective views of support members fitted with stopper members.
Figure 5:
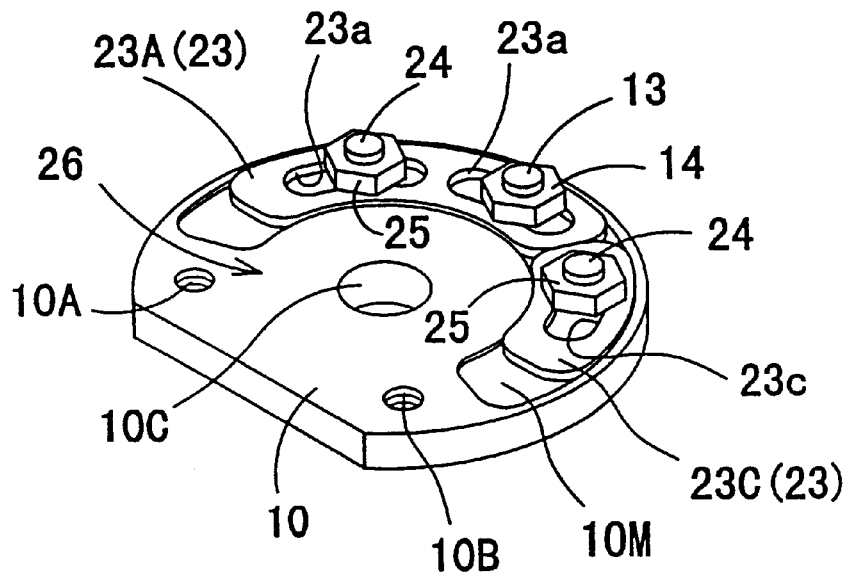

First describing the connection structure for connecting the calf rear cuff 2 to the foot sole plate 3, as shown in FIG. 3 and FIG. 5B, a circular and flat foot joint face 2a having a cutaway portion is formed at the lower end of the calf rear cuff 2, and the positioning of a support member 10 relative to the calf rear cuff 2 can be carried out simply by placing the support member 10 which is formed to have substantially the same shape and size as the foot joint face 2a on the foot joint face 2a. While the support member 10 is placed on the foot joint face 2a as described above, two screws 11, 12 (only one of them is shown in FIG. 3) are inserted into through holes 2C, 2C formed in the calf rear cuff 2 from the rear side and screwed into tapped holes 10A, 10B formed in the support member 10, respectively, and a bolt 13 for fixing a stopper which projects from the calf rear cuff 2 (not shown in the figure) and will be described hereinafter and a nut 14 to be mated with the end of the bolt 13 are tightened together to fix the support member 10 to the calf rear cuff 2 at three locations. A female screw 15 having a threaded portion 15A on the inner surface of an axial portion is inserted into a through hole 2D formed in the calf rear cuff 2, an axial hole 10C formed in the center portion of the support member 10 and a through hole 3C formed in the adjoining side end portion of the foot sole plate 3 in the order named from the rear side, and a male screw 16 is screwed into the threaded portion 15A of the female screw 15 from the front side through the through hole 3C to support the foot sole plate 3 in such a manner that it can turn on the axial core X of the male screw 16. The foot sole plate 3 is rotatably supported by the support member 10 and the calf rear cuff 2. However, the foot sole plate 3 may be rotatably supported by the support member 10 alone. The axial core X, that is, the rotational center of the foot sole plate 3 is set to the same height as the height H in a vertical direction of the biophysiological ankle joint axis (also called ankle joint axis) as shown in FIG. 2C and to a position which it intersects a vertical line shown in the figure, that is, a substantially central position in a horizontal direction. It is optimal to set the rotational center X of the foot sole plate 3 as shown in the figure but the position may be shifted slightly. Fixing tools for fixing the support member 10 to the lower end of the calf rear cuff 2 are the bolt 13 for fixing a stopper, the nut 14 to be mated with the end of the bolt 13, and two screws 11, 12 to be screwed into the tapped holes 10A, 10B. These may be freely changed.

Figure 4:
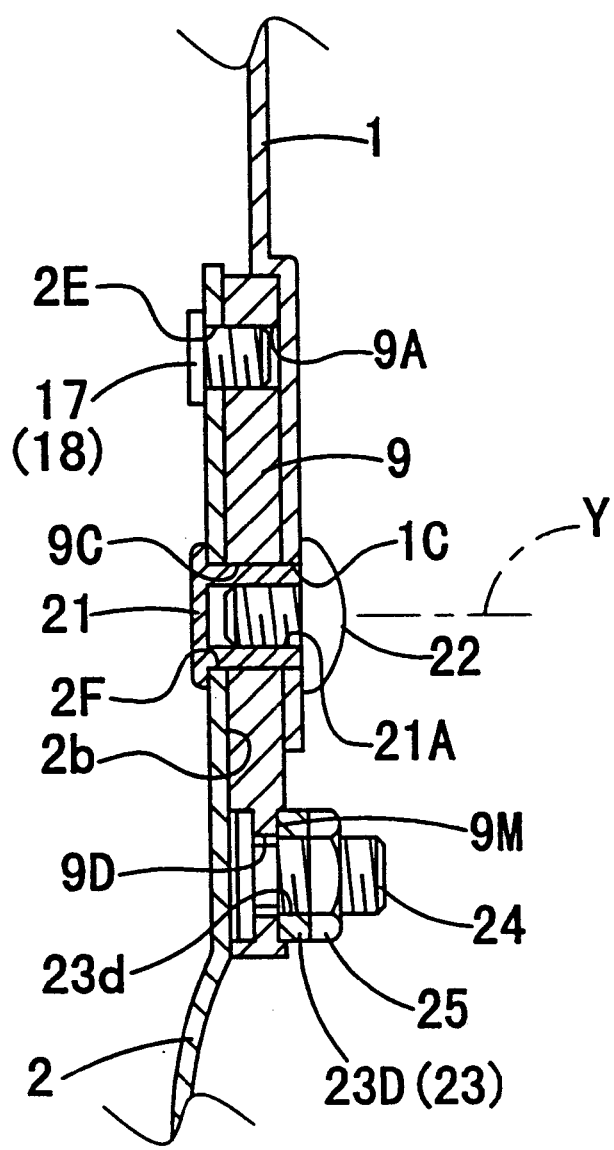
FIG. 4 is a longitudinal side view showing a connector between the thigh front cuff and the calf rear cuff.

The connection structure for connecting the calf rear cuff 2 to the thigh front cuff 1 is the same as the connection structure for connecting the calf rear cuff 2 to the foot sole plate 3. That is, as shown in FIG. 4 and FIG. 5A, a circular and flat knee joint face 2b is formed at the upper end of the calf rear cuff 2, and the positioning of a support member 9 relative to the calf rear cuff 2 can be carried out simply by placing the support member 9 which is formed to have substantially the same shape and size as the knee joint face 2b on the knee joint face 2b. While the support member 9 is placed on the knee joint face 2b at the upper end of the calf rear cuff 2 as described above, two screws 17, 18 (only one of them is shown in the figure) are inserted into through holes 2E, 2E formed in the calf rear cuff 2 from the rear side and screwed into tapped holes 9A. 9B formed in the support member 9, and a bolt 19 for fixing a stopper which will be described hereinafter and projects from the calf rear cuff 2 (not shown in the figure) and a nut 20 to be mated with the end of the bolt 19 are tightened together to fix the support member 9 to the calf rear cuff 2 at three locations. A female screw 21 having a threaded portion 21A on the inner surface of an axial portion is inserted into a through hole 2F formed in the calf rear cuff 2, an axial hole 9C formed in the center portion of the support member 9 and a through hole 1C formed in the adjoining side end portion of the thigh front cuff 1 in the order named from the rear side, and a male screw 22 is screwed into the threaded portion 21A of the female screw 21 from the front side through the through hole 1C to support the thigh front cuff 1 in such a manner that it can turn on the axial core Y of the male screw 22. The thigh front cuff 1 is rotatably supported by the support member 9 and the calf rear cuff 2. However, the thigh front cuff may be rotatably supported by the support member 9 alone. The axial core Y, that is, the rotational center of the thigh front cuff 1 is set to the same height as the height h in a vertical direction of the biophysiological knee joint axis as shown in FIG. 2C and to a position which it intersects a vertical line shown in the figure, that is, a substantially central position in a horizontal direction. It is optimal to set the rotational center Y of the thigh front cuff 1 as shown in the figure but the position may be shifted slightly. Fixing tools for fixing the support member 9 to the upper end of the calf rear cuff 2 are the bolt 19 for fixing a stopper, the nut 20 to be mated with the end of the bolt 19, and the two screws 17, 18 to be screwed into the tapped holes 9A, 9B. These may be freely changed.

Describing the support member 10 out of the above support members 9, 10 in detail, as shown in FIG. 3 and FIG. 5B, a 180° or more (may be 180° or less) arc slide groove 10M is formed on the surface of the support member 10, a fan-like stopped member 23 whose lower end is mated with the slide groove 10M can slide along the slide groove 10M and is provided with a bolt 24 and a nut 25 to be mated with the bolt 24 as fixing tools for fixing the stopper member 23 to the support member 10 such that it cannot move. FIG. 5B shows that the stopper member 23 has three stopper members 23A, 23B, 23C shown in FIGS. 6A to 6C which are used alone or in combination to switch among various states that will be described later. Long holes 23a, 23a, 23b, 23c are formed in these stopper members 23A, 23B, 23C in a longitudinal direction and the positions of the stopper members can be changed within these long holes 23a, 23a, 23b, 23c, respectively. Since the attachment structures of all the stopper members 23A, 23B, 23C are the same, the attachment structure of one stopper member 23C will be described. As shown in FIG. 3, the bolt 24 is inserted into the through hole 10D formed in the support member 10 and the long hole 23c of the stopper member 23C from the rear side of the support member 10, the nut 25 is mated with the end of the bolt 24 to fix the stopper member 23C to the support member 10, and the stopper member 23C can be moved to be adjusted within the range of the long hole 23c by loosening the mated nut 25.

Describing the other support member 9 in detail, as shown in FIG. 3 and FIG. 5A, a 180° or less (may be 180° or more) arc slide groove 9M is formed on the surface of the support member 9, and a fan-like stopper member 23 whose lower end is mated with the slide groove 9M can slide along the slide groove 9M and is provided with a bolt 24 and a nut 25 to be mated with the bolt 24 as fixing tools for fixing the stopper member 23 to the support member 9 such that it cannot move. The stopper member 23 is a stopper member 23D shown in FIG. 6D, a long hole 23d extending in a longitudinal direction is formed in this stopper member 23D, and the position of the stopper member can be changed within the range of the long hole 23d. When the attachment structure of the stopper member 23D is described, as shown in FIG. 4, the bolt 24 is inserted into a through hole 9D formed in the support member 9 and the long hole 23d of the stopper member 23D from the rear side of the support member 9 in the stated order, the nut 25 is mated with the end of the bolt 24 to fix the stopper member 23D to the support member 9, and the stopper member 23D can be moved within the range of the long hole 23d by loosening the mated nut 25.

As shown in FIG. 2B, FIG. 3, FIG. 4, and FIGS. 5A and 5B, the adjoining side end portion 1T or 3T of the thigh front cuff 1 or the foot sole plate 3 is formed like an arc so that it can enter arc space 26 formed on an inner side of the stopper member 23 projecting upward from the slide groove 9M or 10M, and a contact portion 1S or 3S, 3S for limiting the rotation angle of the thigh front cuff 1 or the foot sole plate 3 when it projects into the traveling path of the stopper member 23 and contacts the stopper member 23 is formed integral with at least one of right and left end portions of the arc adjoining side end portion 1T or 3T.

The angles a to i of the stopper members 23A, 23B, 23C, 23D shown in FIGS. 6A, 6B, 6C and 6D are set as follows. a=43°, b=115°, c=65°, d=15°, e=26°, f=7° g=40°, h=89°, i=105°.

Figure 6:
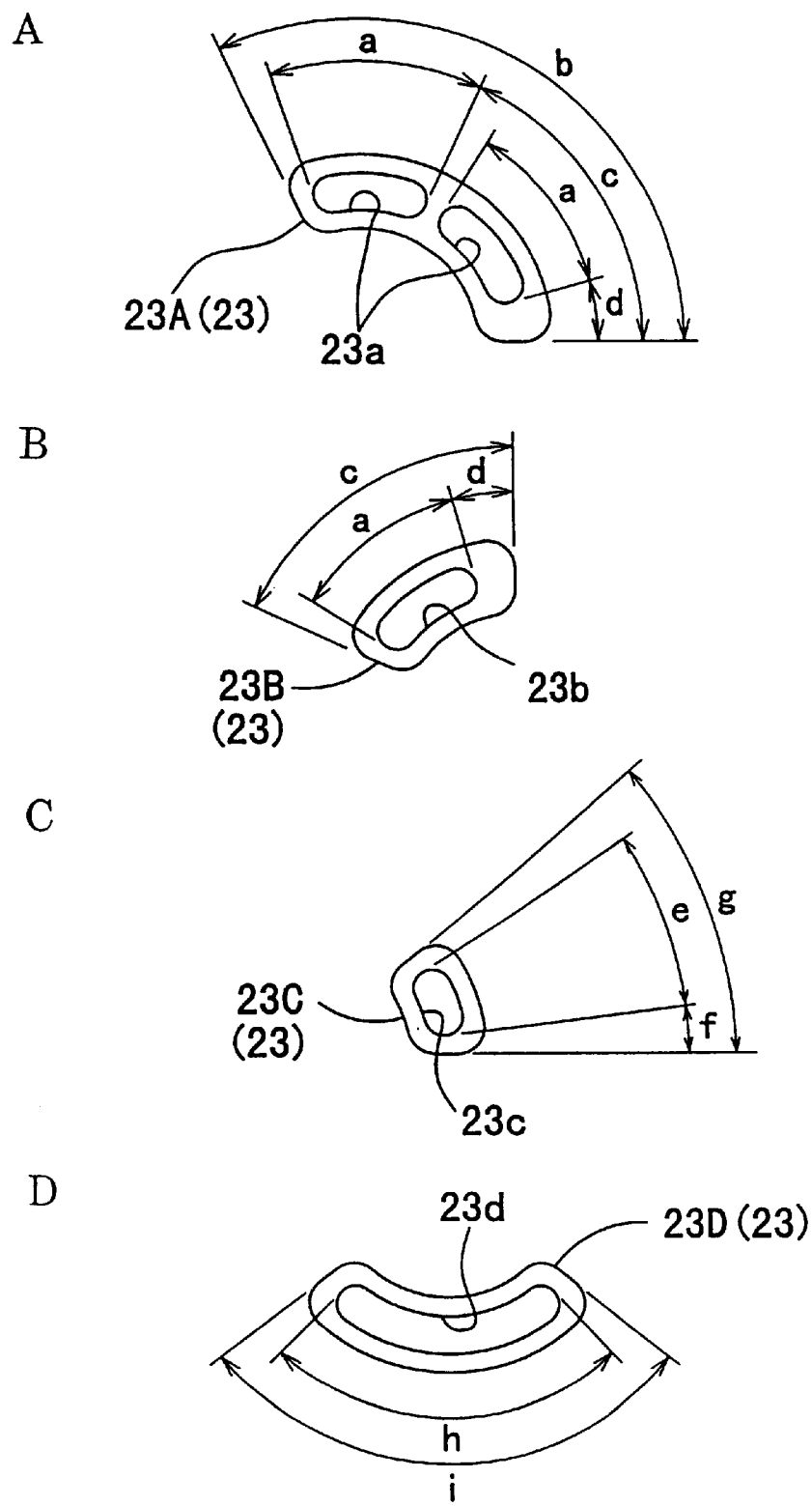
FIGS. 6A, B, C and D are plan views showing the shapes of four different stopper members.
Figure 7:
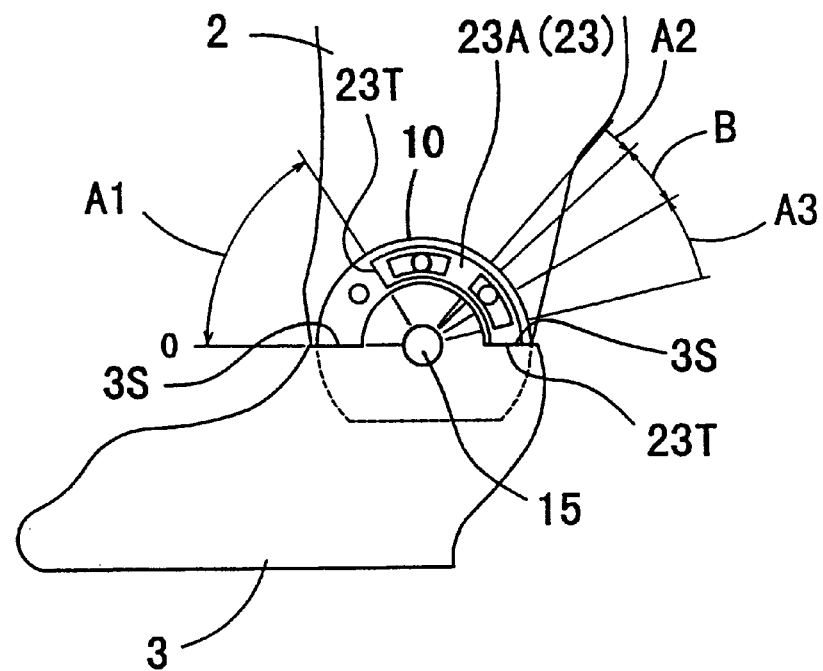
FIGS. 7A and B are diagrams showing the turning adjustable ranges of the stopper members.
Figure 7:
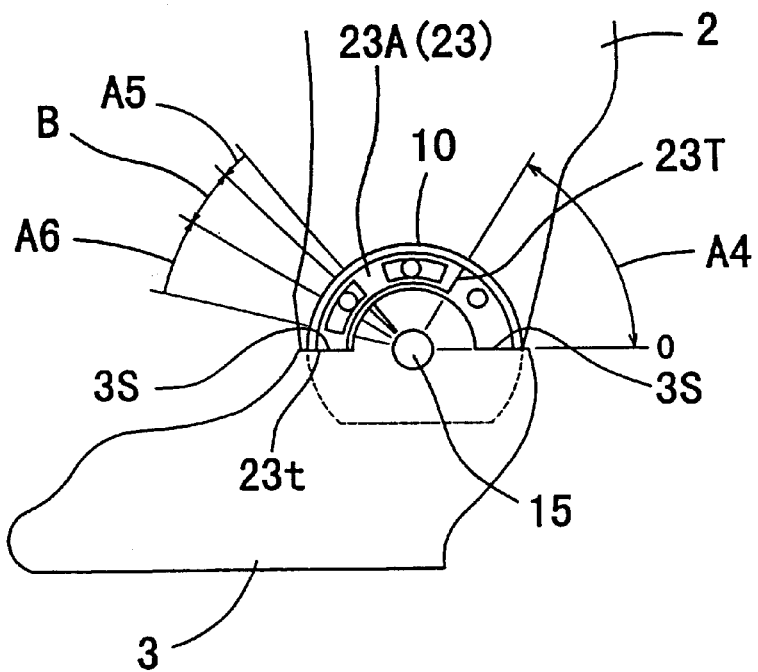

Describing the function of the device when the above stopper members 23A, 23B, 23C, 23D are used, FIG. 7A shows that one end 23T of the fan-like stopper member 23A having a width of 115° shown in FIG. 6A is in contact with the opposing contact portion 3S of the foot sole plate 3, that is, a state for carrying out backward damping. In this case, the backward turning range A1 is 65° and the foot sole plate 3 can turn within a range of 65°. The range A2 in which the stopper member 23A can be turned clockwise from this state is 11° and the range A3 in which the stopper member 23A can be turned counterclockwise from this state is 18°. That is, the position of the stopper member 23A with respect to the foot sole plate 3 can be changed within a range from a backward turning angle adjustable range of 11° to a forward turning angle adjustable range of 18° for backward damping.

In FIG. 7B, the stopper member 23A can function as a forward damping stopper member by merely changing its position. That is, the other end 23t of the stopper member 23A is in contact with the opposing contact portion 3S of the foot sole plate 3, in other words, a state for carrying out forward damping. In this case, the forward turning range A4 is 65° and the foot sole plate 3 can be turned within a range of 65°. The range A6 in which the stopper member 23A can be turned clockwise from this state is 18° and the range A5 in which the stopper member 23A can be turned counterclockwise from this state is 11°. That is, the position of the stopper member 23A with respect to the foot sole plate 3 can be changed within a range from a backward turning angle adjustable range of 11° to a forward turning angle adjustable range of 18° for forward damping.

Figure 8:
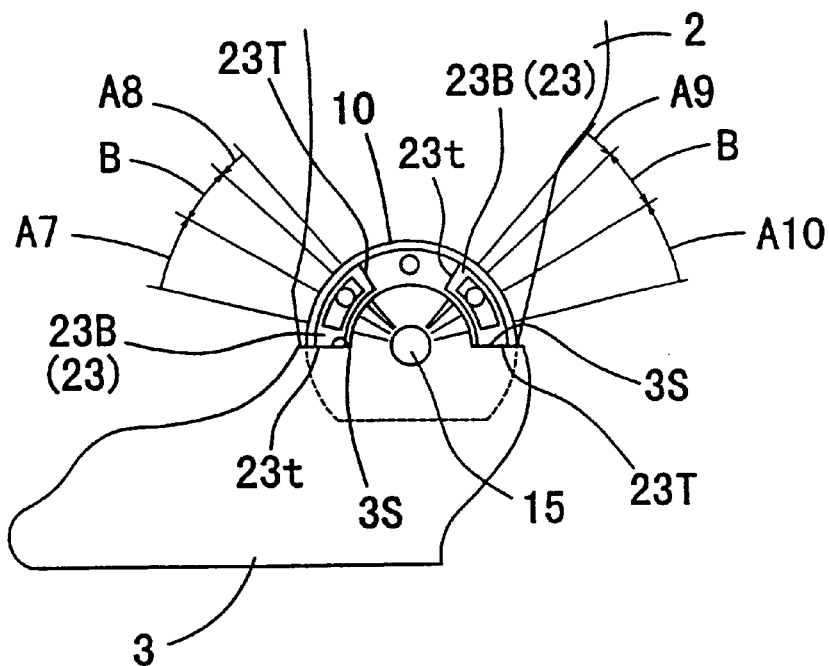
FIGS. 8A and B are diagrams showing the turning adjustable ranges of the stopper members.
Figure 8:
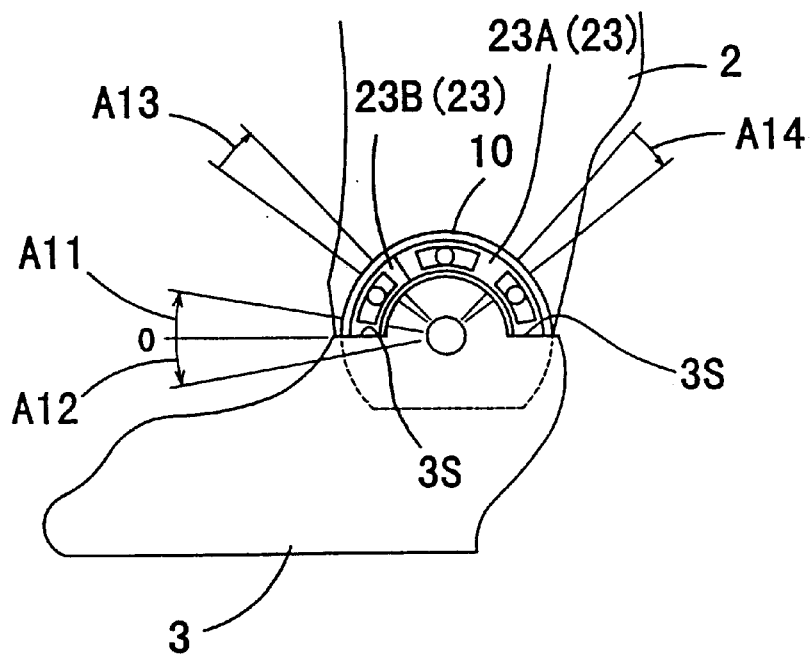

FIG. 8A shows that one end portions 23T, 23t of the two fan-like stopper members 23B having a width of 65° shown in FIG. 6B are in contact with the contact portions 3S, 3S of the foot sole plate 3, that is, a state that the foot sole plate 3 cannot be rotated (fixed). The range A7 in which the front stopper member 23B can be turned clockwise from this state is 18° and the range A8 in which the front stopper member 23B can be turned counterclockwise from this state is 11°. The range A9 in which the rear stopper member 23B can be turned clockwise is 11° and the range A10 in which the rear stopper member 23B can be turned counterclockwise is 18°. That is, both backward and forward dampings can be carried out by changing the positions of the stopper members 23B, 23B within a range from a backward turning angle adjustable range of 11° to a forward turning angle adjustable range of 18° for forward damping and within a range from a backward turning angle adjustable range 11° to a forward turning angle adjustable range of 18° for backward damping from the unrotatable state (fixed state), respectively. Letter B shown in FIGS. 7A and 7B and FIG. 8A denotes an angle occupied by the bolt 24 in the long hole, which is 14°. The adjustable range can be changed by changing this angle.

FIG. 8B shows that the fan-like stopper member 23A having a width of 115° and the fan-like stopper member 23B having a width of 65° shown in FIG. 6A are arranged such that the foot sole plate is completely unrotatable (fixed). In this case, the range A11 in which the two stopper members 23A, 23B can be turned clockwise is 11° and the range A12 in which the two stopper members 23A, 23B can be turned counterclockwise is 11°. That is, the positions of the two stopper members 23A, 23B with respect to the foot sole plate 3 can be changed within a range from a forward turning angle of 11° to a backward turning angle of 11°. As the minimum movable ranges A13, A14 shown in the figure are both 11° in this case, positioning of the two stopper members 23A, 23B are limited to a range from a forward turning angle of 11° to a backward turning angle of 11°.

Figure 9:
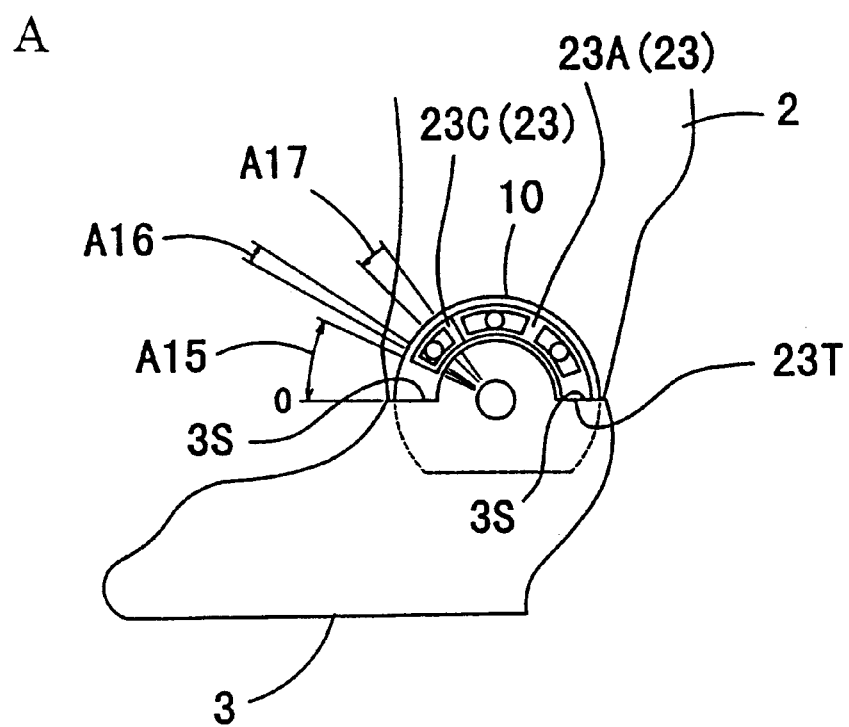
FIGS. 9A and B are diagrams showing the turning adjustable ranges of the stopper members.
Figure 9:
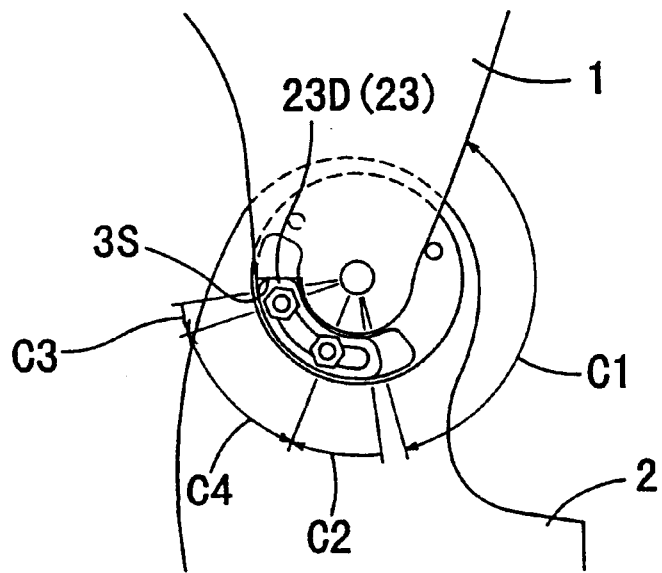

FIG. 9A shows that the fan-like stopper member 23A having a width of 115° and the fan-like stopper member 23C having a width of 40° C. shown in FIGS. 6A and 6C are arranged (see FIG. 5B) and one end 23T of the stopper member 23A is in contact with the contact portion 3S of the foot sole plate 3, that is, a state for carrying out backward damping as in FIG. 7A. In this case, the backward turning range A15 is 25° which differs from the above range, and the foot sole plate 3 can be rotated within a range of 25°. The range A16 in which the stopper members 23A, 23C can be turned clockwise from this state is 1° and the range A17 in which the stopper members 23A, 23B can be turned counterclockwise from this state is 11°. That is, the positions of the stopper members 23A, 23C with respect to the foot sole plate 3 can be changed within a range from a backward turning angle adjustable range of 11° to a forward turning angle adjustable range of 1° for backward damping FIG. 9B shows that the fan-like stopper member 23D having a width of 105° shown in FIG. 6D is arranged and the bending range C1 is 130° within which the thigh front cuff 1 can be rotated with respect to the calf rear cuff 2. The range C2 in which the stopper member 23D can be turned clockwise from this state is 30° C. and the range C3 in which the stopper member 23D can be turned counterclockwise from this state is 10°. That is, the position of the stopper member 23D with respect to the thigh front cuff 1 can be changed within a range from a bending angle of 30° to an over-extension angle of 10°. C4 shown in the figure denotes an area between the bolts 19 and 24.

Figure 10:
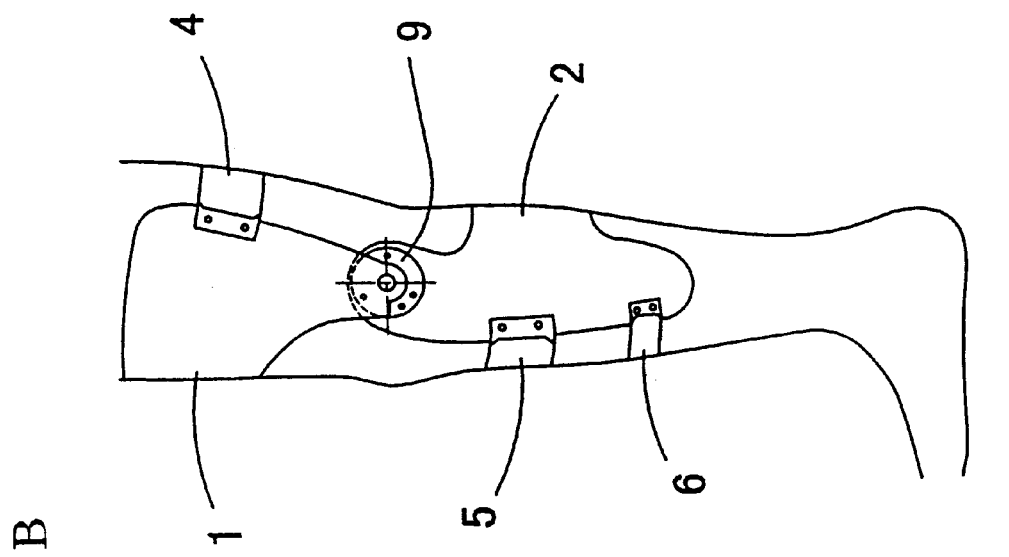
Figure 10:
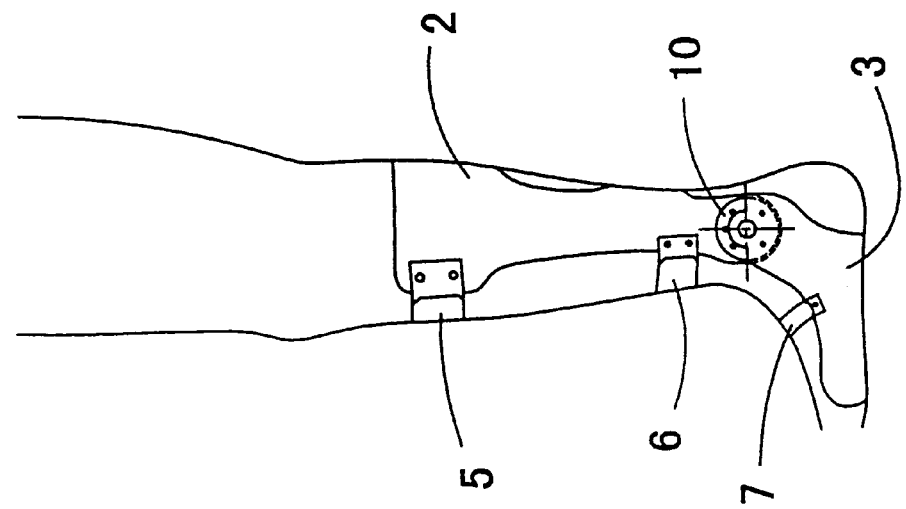

In the above embodiment, a long lower limb joint device constructed by the thigh front cuff 1, the calf rear cuff 2 and the foot sole plate 3 is described. A short lower limb joint device may be constructed by the calf rear cuff 2 and the foot sole plate 3 as shown in FIG. 10A or a knee joint device may be constructed by the thigh front cuff 1 and the calf rear cuff 2 as shown in FIG. 10B.

Figure 11:
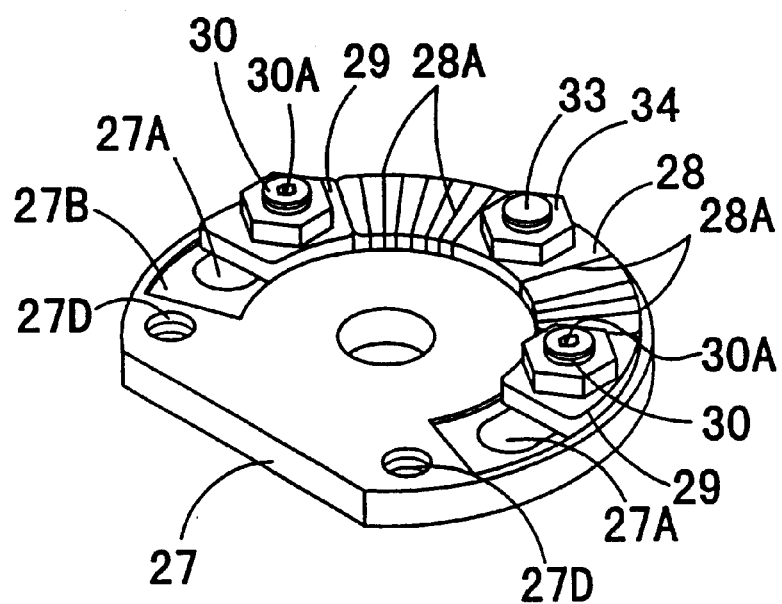
FIG. 11 is a perspective view showing another support member fitted with a stopper member.
Figure 12:
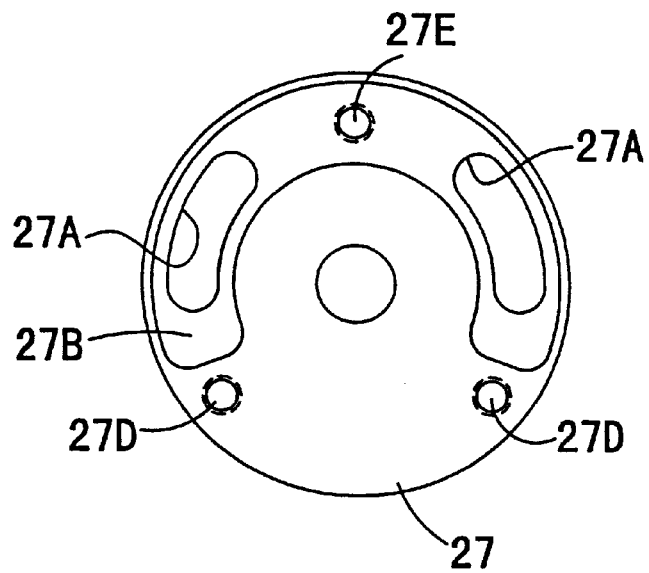
Figure 12:
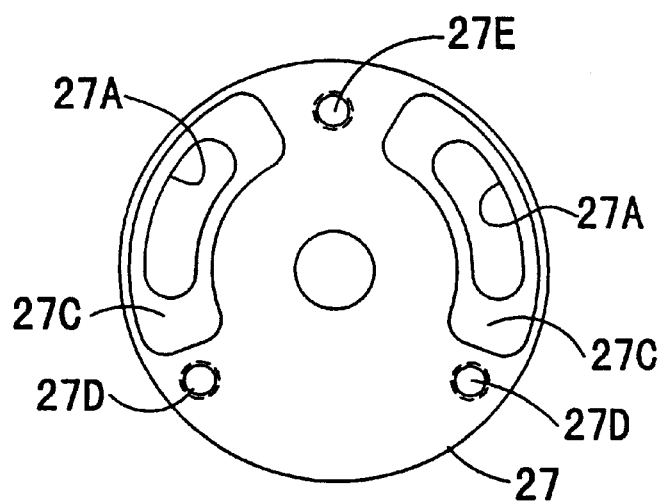
Figure 13:
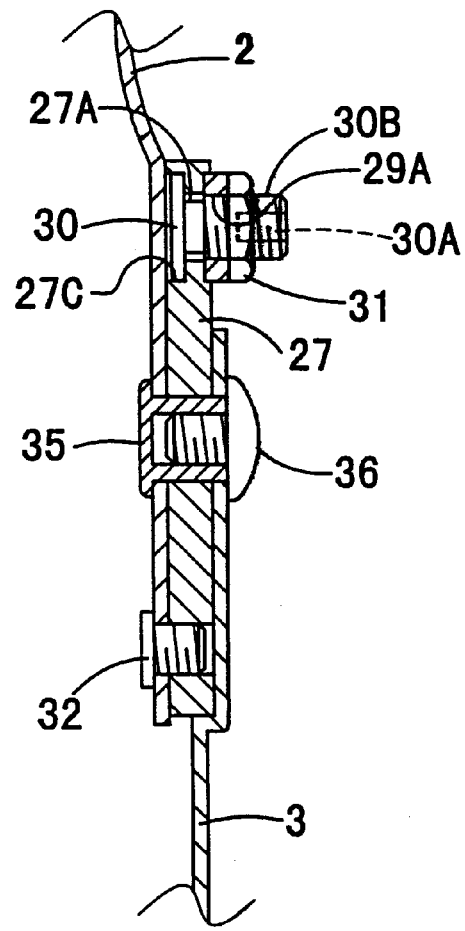
FIG. 13 is a longitudinal side view showing a connector for connecting the calf rear cuff and the foot sole plate by the support member shown in FIG. 10.
Figure 14:
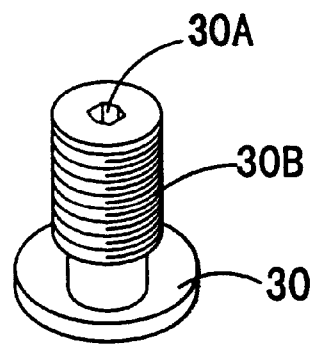
FIG. 14 is a perspective view of a headed screw.
Figure 15:
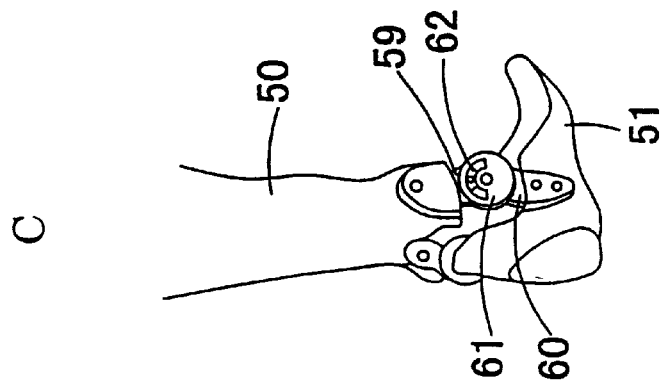
FIGS. 15A to 15C show three artificial limb joint devices of the prior art, wherein FIGS. 15A and B are side views
Figure 15:
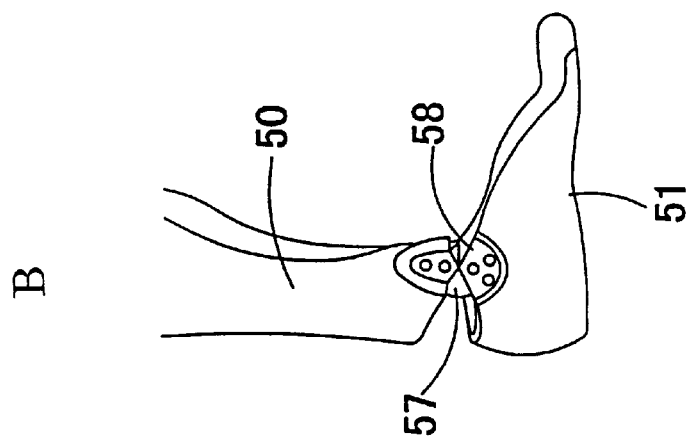
Figure 15:
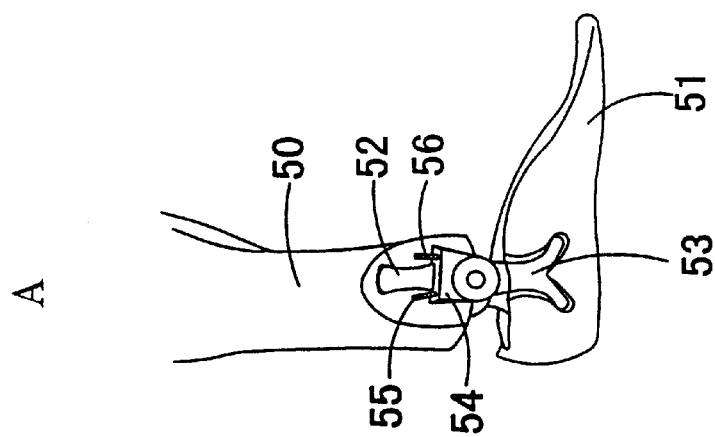

The support members 9, 10 and the stopper member 23 may be constructed as shown in FIG. 11. That is, as shown in FIGS. 12A, 12B and FIG. 13, two arc long holes 27A, 27A are formed in the support member 27, a slide groove 27B with which the lower ends of three stopper members 28, 29, 29 are mated and along which the two stopper members 29, 29 can move is formed in the front side of the support member 27, respectively, a threaded portion 29A to be mated with the end of a headed-screw 30 having a hexagonal hole 30A formed in the center of an axial portion 30B shown in FIG. 14 is formed in each of the stopper members 29, the end of the axial portion 30B of the headed screw 30 is inserted into the long hole 27A of the support member 27 from the rear side, and a hexagonal wrench is inserted into the hexagonal hole 30A from the front side and turned counterclockwise to mate the headed screw 30 with the threaded portion 29A of the stopper member 29 so as to fix the stopper member 29 to the support member 27. Thereafter, a nut 31 is mated with the end of the axial portion projecting from the front side of the stopper member 29 by rotating it clockwise to prevent the headed screw 30 from being loosened. Denoted by 27C shown in FIG. 12B is an arc long groove formed in the rear side of the support member 27 to be mated with the head of the headed screw 30 in such a manner that the headed screw 30 can move therealong. Denoted by 27D, 27D, and 27E shown in FIG. 11 and FIGS. 12A and 12B are screw holes for screw-fixing the support member 27 to the calf rear cuff 2 by means of bolts 32, 32 and 33. A nut 34 for fixing the stopper member 28 to the support member 27 is mated with the head of the bolt 33. 35 and 36 shown in FIG. 13 represent a headed pin for rotatably fixing the foot sole plate 3 to the support member 27 and a screw to be screwed into a threaded portion formed on the inner surface of the headed pin. The stopper member 28 is made from a synthetic resin, for example, and has a large number of grooves 28A . . . so that it can be easily detached as shown in FIG. 11. Therefore, after the stopper member 28 is detached from the support member 27, it is separated along a specific groove 28A out of the above grooves 28A . . . , whereby the stopper member 28 can be made small and the movable ranges of the stopper members 29, 29 can be expanded.

According to the present invention, since the body protecting members are made from a material having flexibility, and the adjoining side end portions of the body protecting members which adjoins to each another in a vertical direction are interconnected by a support member in such a manner that the body protecting members are placed one upon the other in a horizontal direction, sufficient strength can be ensured at connectors even when a conventional joint is eliminated, a torsion load received from the body during walking can be absorbed efficiently by the bending of the body protecting members, the body protecting members can restore their original shapes by restoring force immediately when they do not receive the load, and the artificial limb joint device can be thus optimized.

The rotation angle range of the rotating body protecting member can be adjusted continuously by changing the position of the stopper member along the rotation locus of the contact portion. In addition, by moving the stopper member along the rotation locus of the contact portion, the contact state of the stopper member to the contact portion can be always made the same, the damage or breakage of the contact portion and the stopper member by contact therebetween can be reduced as much as possible, and the artificial limb joint device can be made durable enough to withstand long-time use advantageously.

According to the present invention, simply by arranging the body protecting members, rotation resistance is not provided to the rotating body protecting member, and the rotating body protecting member located on an outer side can be easily rotated and moved smoothly, thereby making it possible to construct a more easy-to-use artificial limb joint device and to prevent without fail a trouble such as the damage of the body which occurs when the rotating body protecting member cannot follow the motion of the body which is in contact with the rotating body protecting member.

According to the present invention, the calcaneus portion at the rear of the foot sole plate and the Achilles' tendon portion at the rear of the lower end portion of the calf rear cuff are made open, thereby making it possible to reduce weight, put on shoes easily and adjust the flexibilities of the foot sole plate and the calf rear cuff.

According to the present invention, the support member is installed on flat and circular knee coupling and foot joint faces formed in the calf rear cuff, thereby making it possible to position the support member and to carry out assembly work easily and quickly.

According to the present invention, since the rotational center of the thigh front cuff is set to substantially the same height as the height in a vertical direction of the biophysiological knee joint axis and the rotational center of the foot sole plate is set to substantially the same height as the height of the biophysiological ankle joint axis, large rotation resistance is not generated in the thigh front cuff and the foot sole plate. Therefore, the knee joint axis and the ankle joint axis of the body can be moved easily and a more easy-to-use artificial limb joint device can be produced.

According to the present invention, the end of the axial portion of the headed screw is inserted into the support member from the rear side, and a wrench or the like is inserted into a hexagonal hole formed in the center of the axial portion from the front side and turned counterclockwise, in other words, against the sun, to mate the support member with the stopper member. The stopper member can be brought close to the head portion of the headed screw and the stopper member is pressed against and fixed to the support member by this mating. After fixing, a nut is mated with the end of the axial portion of the headed screw projecting to the front side from the stopper member by rotating the nut clockwise to prevent the loosening of the headed screw by the nut without fail. Thereby, the position of the stopper member is not changed unexpectedly, and an artificial limb joint device which can be used without anxiety is provided.

According to the present invention, the adjoining side end portions of the thigh front cuff and the foot sole plate can be inserted into arc space formed on the inner top side of the stopper member and the connectors of the thigh front cuff and the foot sole plate can be prevented from being increased in size. The contact portion contacting the stopper member is formed integral with at least one of right and left end portions of the arc adjoining side end portion, thereby making it possible to produce the artificial limb joint device of the present invention more advantageously than an artificial limb joint device in which a separately formed contact portion is attached to the adjoining side end portion.

What is claimed is:

1. An artificial limb joint device comprising body protecting members which adjoin to each other in a vertical direction, one of which can turn with respect to the other body protecting member, wherein
the body protecting members are made from a material having flexibility, a support member for rotatably supporting the adjoining side end portion of a body protecting member is placed on the adjoining side end portion of the other body protecting member, a stopper member which contacts a contact portion provided in the adjoining side end portion of the body protecting member to limit the rotation angle of the body protecting member is slidably mated with an arc slide groove formed on a surface of the support member, at least one long hole is formed in the stopper member in a longitudinal direction thereof, and the position of the stopper member relative to the body protecting member can be changed along the rotation locus of the contact portion and within a range of the long hole so that the rotation angle range of the rotating body protecting member can be adjusted.

2. The artificial limb joint device of claim 1, wherein the unrotating body protecting member out of the body protecting members which adjoin to each other in a vertical direction is arranged on an inner side which is in contact with the body, the support member is placed on the outer surface of the adjoining side end portion of the unrotating body protecting member, and the rotating protecting member the adjoining side end portion of which rotates is rotatably supported by bringing the rotating body protecting member into contact with the outer surface side of the support member.

3. The artificial limb joint device of claim 1, wherein the body protecting members consist of a thigh front cuff, a calf rear cuff and a foot sole plate, and a long lower limb joint device is constructed by interconnecting the adjoining side end portions thereof by the support member.

4. The artificial limb joint device of claim 1, wherein the body protecting members consist of a calf rear cuff and a foot sole plate, and a short lower limb joint device is constructed by interconnecting the adjoining side end portions thereof by the support member.

5. The artificial limb joint device of claim 1, wherein the body protecting members consist of a thigh front cuff and a calf rear cuff, and a knee joint device is constructed by interconnecting the adjoining side end portions thereof by the support member.

6. The artificial limb joint device of claim 3, wherein a calcaneus portion at the rear of the foot sole plate and an Achilles' tendon portion at the rear of a lower end portion of the calf rear cuff are made open.

7. The artificial limb joint device of claims 3 to 5, wherein a flat and circular knee joint face for positioning the support member for supporting the thigh front cuff is formed at the upper end of the calf rear cuff, and a flat and circular foot joint face for positioning the support member for supporting the foot sole plate is formed at the lower end of the calf rear cuff.

8. The artificial limb joint device of claim 3 or 5, wherein the rotational center of the thigh front cuff is set to substantially the same height as the height in a vertical direction of the biophysiological knee joint axis.

9. The artificial limb joint device of claim 3 or 4, wherein the rotational center of the foot sole plate is set to substantially the same height as the height in a vertical direction of the biophysiological ankle joint axis.

10. The artificial limb joint device of claim 1, wherein the support member is formed of a plate-like body to be fixed to the upper and lower end portions of the calf rear cuff, and fixing tools for fixing the stopper member whose lower end is mated with a slide groove formed like an arc on the surface of the plate-like body in such a manner that the stopper member can move along the slide groove and cannot move over the plate-like body are provided.

11. The artificial limb joint device of claim 10, wherein the fixing members consist of a headed screw having a hexagonal hole formed in the center of an axial portion and a nut to be mated with the end of the headed screw, a through hole into which the axial portion of the headed screw is inserted is formed in the support member, a threaded portion to be mated with the axial portion of the headed screw is formed in the stopper member, the end of the axial portion of the headed screw is inserted into the support member from the rear side and mated with the stopper member, and the nut is mated with the end of the axial portion projecting from the stopper member.

12. The artificial limb joint device of claim 10, wherein the adjoining side end portions of the thigh front cuff and the foot sole plate are formed like an arc so that they can enter arc space formed on an inner side of the stopper member projecting upward from the slide groove, and the contact portion which projects Into the traveling path of the stopper member and contacts the stopper member is formed integral with at least one of the right and left end portions of each of the arc adjoining side end portions.

13. The artificial limb joint device of claims 2 and 10, wherein the stopper members located at the lower end portion of the calf rear cuff, out of the stopper members mated with the slide grooves, are comprised of a fan-like stopper member having a width of 115°, a backward turning angle of 11° and a forward turning angle of 18°, a fan-like stopper member having a width of 65°, a backward turning angle of 11° and a forward turning angle of 18° and a fan-like stopper member for further fixing these two stopper members, having a width of 40° and an adjustable range of 12°, these three types of stopper members are used alone or in combination of two or more, or a plurality of stopper members of the same type are used to switch among a state for carrying out only backward damping, a state for carrying out only forward damping, a state for carrying out both forward and backward dampings and a fixed state for preventing the rotation of the rotating body protecting member, and the stopper members located at the upper end portion of the calf rear cuff, out of the stopper members mated with the slide grooves, is consisted of a fan-like stopper member for damping the extension of the knee having a width of 105°, a bending angle of 30° and an over-extension angle of 10°.

* * * * *